United States Patent [19]

Muzzarelli

[11] Patent Number: 5,378,472
[45] Date of Patent: Jan. 3, 1995

[54] METHYL PYRROLIDINONE CHITOSAN, PRODUCTION PROCESS AND USES THEREOF

[75] Inventor: Ricardo Muzzarelli, Ancona, Italy

[73] Assignee: Merck Patent Gesellschaft Mit Beschrankter Haftung, Darmstadt, Germany

[21] Appl. No.: 910,159

[22] PCT Filed: Nov. 18, 1991

[86] PCT No.: PCT/EP91/02168
§ 371 Date: Jul. 27, 1992
§ 102(e) Date: Jul. 27, 1992

[87] PCT Pub. No.: WO92/09635
PCT Pub. Date: Jun. 11, 1992

[30] Foreign Application Priority Data

Nov. 26, 1990 [IT] Italy ................... 642-A/90

[51] Int. Cl.[6] .................. A61K 9/70; L08B 37/08
[52] U.S. Cl. .................. 424/445; 424/18.36; 424/402; 424/464; 424/489; 536/20; 536/31
[58] Field of Search ............ 424/445, 402, 489, 78.36, 424/464; 536/20, 31

[56] References Cited

U.S. PATENT DOCUMENTS 5,116,824 5/1992 Miyata et al. .................. 424/445

*Primary Examiner*—Thurman K. Page
*Assistant Examiner*—Peter F. Kulkosky
*Attorney, Agent, or Firm*—Millen, White, Zelano, & Branigan

[57] ABSTRACT

Modified chitins and chitosans with recurring units of the formula

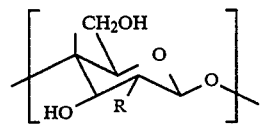

wherein R denotes $-NH_2$, $-NHCOCH_3$ and R', with R' being present in at least 30% of the recurring units, characterized in that R' represents a group of the formula

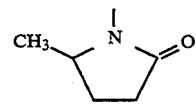

in a proportion of at least 90%.

Due to their favourable biological properties, these materials are advantageously useful in medical and cosmetical applications.

4 Claims, No Drawings

METHYL PYRROLIDINONE CHITOSAN, PRODUCTION PROCESS AND USES THEREOF

SUMMARY OF THE INVENTION

It is an object of the present invention to provide a novel class of water-soluble, modified polysaccharides derived from chitosans, here indicated as 5-methylpyrrolidinone chitosans, where the glucan chains carry, at position 2,5-methylpyrrolidinone pendant groups. An essential characteristic property of 5-methylpyrrolidinone chitosans is their high susceptibility to depolymerization by lyozyze. When 5-methylpyrrolidinone chitosans are applied in vivo to a wound, this characteristic provides an efficient way to stimulate macrophages and spleen cells, and to favor the ordered deposition of collagen, while providing glucosamine and N-acetylglucosamine monomers no the biosynthetic route of hyaluronic acid and glycosaminoglycans. This exceptionally favorable biochemical significance enables 5-methylpyrrolidinone chitosans to heal wounds in connective tissues otherwise difficult or impossible to heal, such as bone and meniscal cartilage. Thus, a further object of the present invention is to provide medical items made of 5-methylpyrrolidinone chitosans, exerting excellent therapeutic effects on human tissues.

Due to the mentioned characteristics, 5-methylpyrrolidinone chitosans are exceptionally useful in cosmetical applications as well. Thus, a further object of the present invention is to provide cosmetical items made of or containing 5-methylpyrrolidinone chitosans.

BACKGROUND OF THE PRESENT INVENTION

The current use of wound dressing materials is based mostly on empirical knowledge rather than on real scientific understanding of the healing process. A certain number of characteristic properties of materials suitable for wound dressing has been clarified. They are: capacity to facilitate removal of exudates and toxic compounds, capacity to maintain humidity at the interface wound tissue/dressing, capacity to permit gas exchange and thermal insulation, protection against secondary infections, easy removal from the wound without damaging the newly formed tissue.

In the course of the last few years, polysaccharide based materials have been made available for wound treatment and general medications; they possess most of the characteristics indicated above while retaining specific properties. Important commercial products are: cross-linked dextran (Debrisan ®, Pharmacia), polyacrylamid agar (Geliperm ®, Geistlich), carboxymethyl cellulose (Comfeel ®), hyaluronic acid (Connettivina ®, Fidia). Very little is known at the histological level about the effects of these polysaccharide based remedies, whilst the clinical data are abundant and the physico-chemical informations are well known. For no one of these dressings, however, a real biological significance is shown. As far as chitin-based wound dressings are concerned, in Japan one product is commercially available (Beschitin ®, Unitika), which is a non-woven fabric manufactured from chitin filaments. So far, no commercial exploitation, has been made of chitosan-based medical items and very limited research has been done in such field.

Previous research on chitin-based wound dressings

Balassa [DE 1,906,155 and DE 1,906,159 (1969); GB 1,252,373 (1971)] showed that pulverized chitin aids wound healing based on observations relating to mechanical resistance of the scar tissue. The same author [U.S. Pat. No. 3,632,754 (1972)] claimed "a process for facilitating wound healing" indicating chitin as "a wound healing accelerator" [also U.S. Pat. No. 3,914,413 (1975)]. In a previous work [Am. J. Surgery, 119, 560–564 (1970)] he indicated that chit in is "physiologically soluble" as a consequence of the effect of lysozyme; even in the absence of histological data, it was suggested that N-acetylglucosamine is important for the orientation and cross-linking of collagen, and that uridine diphosphate N-acetylglucosamine is a key compound in the biosynthesis of hyaluronic acid.

Widra [EP 0,089,152 (1983)] and Miyata et al. [Jpn. Kokai Tokkyo Koho JP 86,141,373 (1986)] described associations of chitosan and keratin or collagen to be applied to a wound in the form of films. Scope of their inventions was to provide medical items corresponding to above listed criteria; they did not however discover any biological or histological effect of chitosan on tissue components.

Yano et al. [Mie Med. J., 35, 53–56 (1985)] cast doubt on the presumed action of chitin on larger collagen production and demonstrated that chitin increases traction resistance compared to controls, but did not increase the collagen quantity in the healing tissues.

Ohshima et al. [Eur. J. Plastic Surg., 10, 66–69 (1987)] reported that wound dressing made of chitin fibers obtained by spinning organic solutions were used on 91 patients and found to be very satisfactory in terms of pain alleviation, adhesion to wound and removal of fluids. Similarly [Jpn. Kokai Tokkyo Koho JP 57,143,508 (1981)], gauzes made of chitin fibers were proposed, for which, however, the physical characteristics only were provided. According to the same applicant [Jpn. Kokai Tokkyo Koho JP 82,11,258 (1982)] they are also useful as binders of fibers of different nature.

Malette and Quigley [U.S. Pat. No. 4,532,134 (1985)] used chitosan acetate salt to heal wounds. They speculated that if fibrin clot formation is avoided, fibroblasts would not be stimulated and cells could replicate the lost tissue and reduce thickness of scar tissue. They also observed reduced callus formation in the healing of bone in dogs.

It is apparent from the above literature, as well as from the study of pertinent scientific evidence so far produced, that modified chitosans have not yet been considered for the medication of wounds, burns and other affections, in the various possible forms such as gauzes, membranes, films, non-woven fabrics, pads, fleeces, gels, not only made of a modified chitosan alone, but not even containing an association of a modified chitosan and other suitable materials. It is also apparent that modified chitosans have never been used on patients.

The prior art, therefore, does not disclose how to improve the biodegradability of amorphous chitin administered to the human body, nor how to heal certain connective tissues, such as bone and meniscal cartilage whose treatment has challenged not only chitins and chitosans but also most of the remedies so far proposed. The prior art does not disclose how to heal wounded or infected tissues in aged patients suffering also from systemic diseases limiting their capacity to heal a wound.

An explanation of the absence of studies on the use of modified chitosans on the human body is the insolubility of modified chitosans in the physiological pH range, and the absence of gel forming ability in most of them, these factors being a new kind of limitation against their use in wound dressing. For instance, N-carboxymethyl chitosan and glutamate glucan from crab chitin are insoluble [Muzzarelli and Zattoni, Intl. J. Biol. Macromol., 8, 137–143 (1986); Muzzarelli, U.S. Pat. No. 4,835,265 (1986)], as well as other modified chitosans in the form of monosubstituted amides carrying carboxyl functions and obtained from organic anhydrides [Muzzarelli et al., Chitin in Nature and Technology, Plenum, New York, 1986]; the same holds for non-functionalized amide such as N-stearoyl and N-decanoyl chitosans [Hirano and Tokura, Chitin and Chitosan, p. 71, Jpn. Soc. Chitin, Saporo, 1982]. Chitosan derivatives carrying sugar moieties still yield gels, due to chain associations, mostly hydrogen bond formation [Yalpani et al., Macromolecules, 17, 272–281 (1984)]. All of the N-alkyl chitosans studied (secondary amines) are gels [Muzzarelli et al., J. Membr. Sci., 16, 295–308 (1983)], and N-alkylidene chitosans (6 to 12 carbon atoms) are insoluble [Kurita et al., Intl. J. Biol. Macromol., 10, 124–125 (1988)].

The only water-soluble modified chitosan so far reported is N-carboxybutyl chitosan, obtained from chitosan and levulinic acid [Muzzarelli et al., Carbohydr. Polymers, 11, 307–320 (1989)]; those authors, however, did not teach the application of N-carboxybutyl chitosan to the human body for medical purposes.

On the other hand, the introduction of certain novel functions into chitosan deprives chitosan of certain desirable characteristics; for example, inorganic esters of chitosan, such as chitosan sulfate esters are deprived of film-forming capacity and bacteriostatic capacity (Muzzarelli et al., Carbohyr. Res., 126, 225–231 (1984)], which are well assessed characteristic properties of plain chitosan and which are desirable properties of a modified chitosan to be used as a medical material.

Aspects indicating that the pyrrolidinone function is desirable in medical items Aspects which make the presence of the pyrrolidinone function desirable in medical materials are the following, and arise mainly form information on poly(-vinylpyrrolidone), a widely used product.

a) Pyrrolidone has the same ring of proline and hydroxyproline which are monomeric unit of gelatin; in polymers it is deprived of the hydrogen atom on the ring nitrogen. Monomeric units carrying a pyrrolidone moiety are therefore unable to form hydrogen links, and pyrrolidone polymers should be superior to gelatin in behavior. Poly(vinylpyrrolidone) exists in fact as a viscous solution (not a gel) and imparts hydrophilicity. Lack of hydrogen bonds permits to expose no water the =N—C(R-)=O functions acting on the solvent capacity of water itself [Ling, In Search of the Physical Basis of Life, p. 176, Plenum Press, New York, 1984].

b) It is known that poly(vinylpyrrolidone), a non-ionic polymer, does not produce inflammation when applied to the cornea in the rabbit and it is biocompatible [Gebelein and Carraher, Bioactive Polymeric Systems, p. 24, Plenum Press, New York, 1985].

c) The poly(vinylpyrrolidone) is a filmogenic substance used to reinforce membranes, either as a mixture or as a copolymer [Gebelein and Carraher, Bioactive Polymeric Systems, p. 144, Plenum Press, New York, 1985].

d) A coating made of poly(vinylpyrrolidone) imparts biocompatibility, thus poly (vinylpyrrolidone) has been tried on patients in associations with various drugs [Chiellini and Giusti, Polymers in Medicine, p. 188, Plenum Press, New York, 1983].

e) Water-alcohol mixtures are solvents for poly(-vinylpyrrolidone), to be used as a binder of pigments in liners, mascara, lipsticks and other cosmetics, besides shampoos. It is also an ingredient of sprays for hair care. Pyroglutamic acid and its salts and esters, which contain a pyrrolidone ring, are widely used in cosmetics [Proserpio, Eccipienti, Sinerga, Milano, 1985].

The prior art, however, does not disclose the introduction of pyrrolidinone or substituted pyrrolidinone ring into a polysaccharide as a covalently bound side-chain, and the use of such products in medical and cosmetic applications.

DETAILED DESCRIPTION OF THE PRESENT INVENTION

It is, therefore, an object of the present invention to provide modified chitins and chitosans with recurring units of the formula

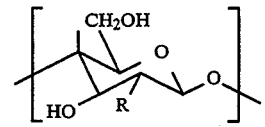

wherein R denotes $-NH_2$, $-NHCOCH_3$ and R' with R', being present in at least 30% of the recurring units, characterized in that R' represents a group of the formula

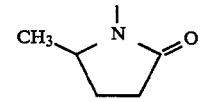

in a proportion of at least 90%.

Furthermore, it is an object of the present invention to provide a chemical process for the production of the modified chitins and chitosans as characterized above.

Finally, it is an object of the present invention to provide medical and cosmetical items made of or containing the modified chitins and chitosans as characterized above.

The advantageous aspects of the present invention are essentially based on:

1) a novel synthetic route to modified chitosans carrying 5-methylpyrrolidinone moieties, named 5-methylpyrrolidinone chitosans;
2) high suspectibility of 5-methylpyrrolidinone chitosans to the hydrolytic action of lysozyme, leading to enhanced biological significance and effects when applied to wounded parts of the human body for medical purposes;
3) enhanced functional effects when applied to healthy parts of the human body for cosmetic purposes.

Chemical aspects of 5-methylpyrrolidinone chitosans

According to the present invention, it was surprisingly found that the reaction between chitosan and levulinic acid can be conducted in such a way as to form N-substituted anhydroglucosidic units where the nitrogen atom is in common to both the glucosamine and the 5-methylpyrrolidinone chitosan moieties. This can be achieved by adopting experimental conditions drastically different than those indicated by previous art, namely much higher chitosan concentration, typically 20 g/l for high molecular weight chitosans, 50 g/l for medium molecular weight chitosans; higher pH values during the hydrogenation step, typically 5.6; higher atomic hydrogen concentration, typically 70 g/l of sodium borohydride, or by performing catalytic hydrogenation with hydrogen gas; prolonged hydrogenation time, at least 3 hours. The reaction temperature may be chosen between 20 and 60° C., preferably at about 25° C. Thanks to the hydrogen mobility on the nitrogen atom, justified by the tautomery between ketimine and enamine under suitable experimental conditions, the carboxyl group eliminates water thus yielding a stable lactam which lends itself to facile hydrogenation in the alpha-beta positions (see reaction scheme 1). The reaction may be carried out under essentially the same conditions but employing pseudo levulinic acid, angelica lactone or levulinate esters (see reaction scheme 2) as starting materials. When employing levulinate esters which are unable to dissolve the chitosan powders, the latter is preliminarily dissolved in an organic acid, such as, preferably, acetic acid.

SCHEME 1
REACTION SCHEME FOR 5-METHYLPYRROLIDINONE CHITOSANS

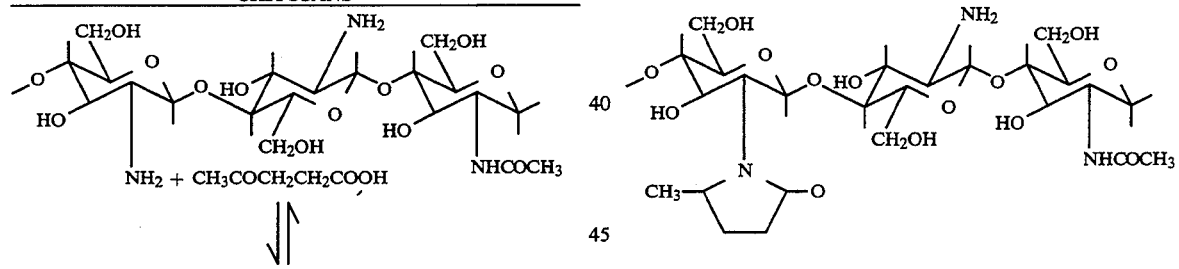

SCHEME 1
REACTION SCHEME FOR 5-METHYLPYRROLIDINONE CHITOSANS
-continued

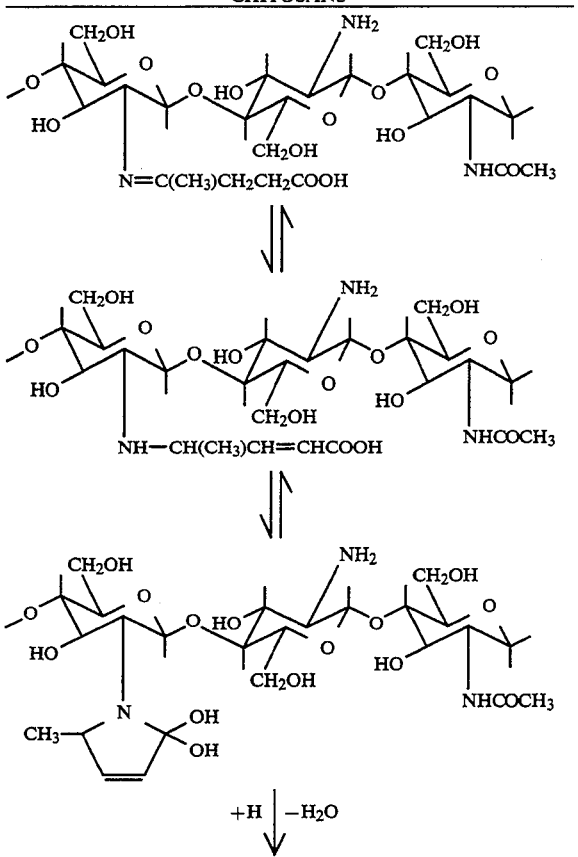

SCHEME 2
SYNTHETIC ROUTES TO 5-METHYLPYRROLIDINONE CHITOSANS
$R^1$ = chitosan (at C2 position)
$R^2$ = alkyl

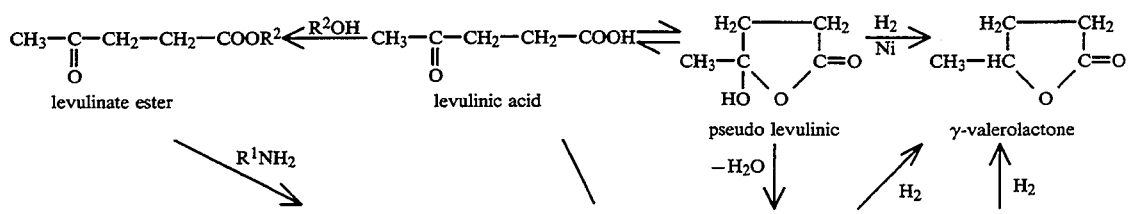

-continued
SCHEME 2
SYNTHETIC ROUTES TO 5-METHYLPYRROLIDINONE CHITOSANS
R¹ = chitosan (at C2 position)
R² = alkyl

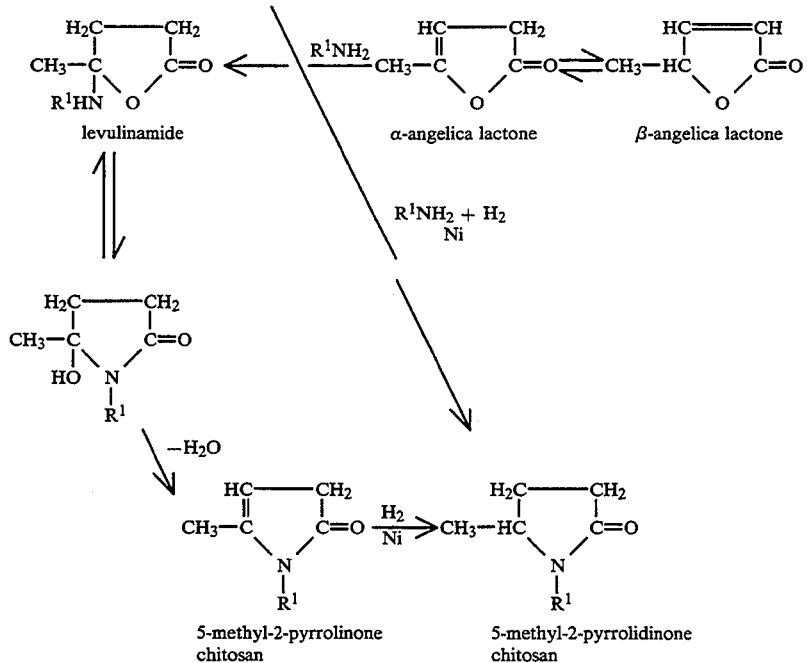

5-methyl-2-pyrrolinone chitosan 5-methyl-2-pyrrolidinone chitosan

The modification of chitosan to disubstituted amide is a novel aspect of the present invention, especially when levulinic acid is used for such a purpose. A further aspect of novelty of the present invention is the proper simultaneous combination of the experimental conditions needed for the production of 5-methylpyrrolidinone chitosans. Whilst the literature concerning levulinic acid reports the capacity of levulinic acid to produce cyclic compounds identified as lactams, with formation of the pyrrolidone ring [R. H. Leonard, Ind. Engin. Chem., 48, 1330–1341 (1956); M. Kitano et al., Chem. Econ., Engin. Rev., 7, 25–29 (1975); W. L. Shilling, Tapppi, 47, 105A–108A (1965)], such publications did not, however, indicate the possibility of lactam ring formation by levulinic acid reacted with chitosans, such a possibility, though hypothesized, having technically and experimentally escaped to many authors for decades. The formation of the 5-methylpyrrolidinone moiety in the modified chitosan, achieved in the context of the present invention by adopting an unusual see of experimental conditions, is an novel alternative to the formation of the N-carboxybutyl group [R. Muzzarelli et al., Carbohydr. Polymers 11, 307–320 (1989); R. Muzzarelli, U.S. Pat. No. 4,835,265 (1986)]. In fact, such prior art produces N-carboxybutyl chitosan and demonstrates its identity, without providing any suggestions for the alternative production of 5-methylpyrrolidinone chitosan. Although the first of the aforementioned publication indicated that part of the N-carboxybutyl function was believed to exist in the 5-methylpyrrolidinone form, exact analytical investigations meanwhile showed that this form, due to the reaction conditions of the synthesis, was generated only in a very low proportion, i.e. in less than 10%. N-Carboxybutyl chitosan, as described in the aforementioned prior art, was obtained at low chitosan concentration (6 g/l) and at a low pH value (4.0), moreover, the hydrogenation step was short and the reducing agent was mild (sodium cyanoborohydride). These conditions are very far from those which allow lactam formation, and possibly do not even permit full substitution, i.e. less than 30%, a major proportion of the repeating units of the N-carboxybutyl chitosan still being in the free amine form.

On the opposite, the conditions adopted in the present process do not only lead to formation of cyclic (lactam) moieties, but also to higher degrees of substitution, i.e. at least 30%. Therefore, according to the present invention, modified chitins and chitosans are obtained where the carbon-2 atoms in the recurring units carry —NH₂, —NHCOCH₃ and R', with R' being present in at least 30% of the recurring units, characterized in that R' represents a group of 5-methyl-2-pyrrolidone in a proportion of at least 90%. The hereby reported 5-methylpyrrolidinone chitosan is an unique and novel macromolecular compound which should not be confused with the chitosan pyroglutamate salt (Kytamer ®, Amerchol) the latter being simply a mixture of chitosan (a macromolecule) and pyroglutamic acid (independent monomers).

The instrumental evidence testifying the identity of 5-methylpyrrolidinone chitosan is the following:

a) Behavior towards metal ions

When 5-methylpyrrolidinone chitosan is titrated with sodium hydroxide or potassium hydroxide, just 9% of the stoichiometric quantity of alkali metal ion, referred to theoretical carboxyl group, combines with the 5-methylpyrrolidinone chitosan. This fact demonstrates that the carboxyl group exists as such [—COOH] to a very limited extent. Being unable to form sodium and potassium salts, the carboxyl group appears to be engaged in lactam ring formation. As a confirmation, the alkalimetric titration according to Broussignac gives an amine titer much lower than the one corresponding to the chitosan used. As for transition metal ions, while N-carboxybutyl chitosan exerts chelating action towards copper and lead, 5-methylpyrrolidinone chitosan shows a limited and a specific complexing ability towards copper alone.

b) Proton nuclear magnetic resonance spectrometry

Authentic methyl pyrrolidinone shows two twin signals at 1.113 and 1.144 ppm in the spectrum, besides signals at 2.2 and 3.7; said signals do not appear in the spectrum for authentic levulinic acid which is flat in the region 0–2 ppm and has one signal at 2.176 ppm followed by two sets of triplets centered an ca. 2.55 and 2.80 ppm. In the spectrum for N-carboxybutyl chitosan the signals corresponding to those of levulinic acid can be found in addition to the broad signal for chitosan, whilst in 5-methylpyrrolidinone chitosan the signals corresponding to the methyl pyrrolidinone characterize the spectrum and are accompanied by lower signals for levulinic acid, which evidently form a salt with the remaining unmodified primary amine. This is in agreement with data published on levulinic acid [Sunjic et al., Kem. Ind. (Zagreb), 33, 599–602 (1984)].

c) $^{13}C$ Nuclear magnetic resonance spectrometry

These spectra for 5-methylpyrrolidione chitosan reveal signals in the interval 20–40 ppm assigned to methyl and methylene groups newly introduced with levulinic acid, in agreement with data reported for poly(vinylpyrrolidone) [D. A. Brant, Solution Properties of Polysaccharides, p. 127, ACS, Washington, 1981] and those reported for authentic levulinic acid [V. Sunjic et al., Kem. Ind. (Zagreb), 33, 599–602 (1984)]. The signal for the carboxyl group is hardly visible, its height being less than twice the background noise. For N-carboxybutyl chitosan, on the other hand, the carboxyl group give sharp signals at 174 and 182 ppm. Different ratios between the methylene signals also reveal a different chemical environment in the linear side chain.

d) Fourier transform infrared spectrometry

For 5-methylpyrrolidione chitosan samples examined in the form of a thin film prepared at pH 6, bands at 1400 $cm^{-1}$ for methylene and methyl groups, at 1690 for the lactam and at 1700 for the amide carbonyl reveal the altered structure of the polysaccharide; moreover, the free amine band at 1590 is depressed [for assignments, A. Wochowics et al., Acta Polym. (Varsavia), 38, 194–189 (1987)]. A comparison of this spectrum with the one for N-carboxymethyl chitosan, which certainly is exempt of cyclic side structures [R. Muzzarelli et al., Carbohydr. Res., 107, 199–214 (1982), FIG. 3] showed that the major difference is certainly in the region 1500–1600 $cm^{-1}$, indicative of the prominence of the lactam band for 5-methylpyrrolidionone chitosan. Also, for protonated thin films of 5-methylpyrrolidione chitosan, the absence of the 1730 $cm^{-1}$ band indicated absence of protonated carboxyl groups.

e) Biodegradability by lysozyme

The hydrolytic depolymerization of 5-methylpyrrolidinone chitosan by hen egg white lysozyme was studied in vitro. Viscometric measurements at three temperatures (25°, 37° and 50° C.) and five 5-methylpyrrolidinone chitosan concentrations (from 9 to 27.3 g/l), provided kinetic data including the Michaelis constant, $1 \times 10^{-4}$ mmol/l. Linearity was observed when log $K_M$ was plotted versus 1/T. The viscosity decrease over 50 min period was a linear function of temperature, independent of initial substrate concentration. Therefore, 5-methylpyrrolidinone chitosan is highly susceptible to the hydrolytic action of lysozyme and its initial high average molecular weight (ca. $700 \times 10^3$ dalton) was decreased down to values close to $10 \times 10^3$ dalton. In comparison with chitosan, it was surprisingly found, according to the present invention, that 5-methylpyrrolidinone chitosan was much more sensitive to the lysozyme action. In fact, chitosans with average molecular weights in the range $166–191 \times 10^3$ were degraded by lysozyme down to values in the range $19–79 \times 10^3$ after 30 hours [Yomota et al., Yakugaku Zasshi, 110, 442–446 (1990)] and the decrease of viscosity in 50 min was just in the range 30–35% for chitosans of similar degree of deacetylation. Fully deacetylated chitosans were found not to be hydrolyzed by lysozyme at physiological pH values. The uniquely high susceptibility of 5-methylpyrrolidinone chitosan to depolymerization by lysozyme, here described for the first time, is a key factor for the surprising favorable results in wound healing.

Biological significance

The most important and surprising biological activities exerted by 5-methylpyrrolidinone chitosan on human tissues, according to the present invention, here described for the first time, are the following, among others: healing of wounded meniscal tissues, healing of decubitus ulcers, depression of capsule formation around prostheses, limitation of scar formation and retraction during healing, and osteoconduction. For each of these topics, details are given below in the Examples section.

The rationale for the use of 5-methylpyrrolidinone chitosan is mainly based on its surprisingly high and unmatched susceptibility to lysozyme hydrolytic action. Once applied to a wound, 5-methylpyrrolidinone chitosan becomes immediately available in the form of oligomers produced under the action of lysozyme, for the following actions:

a) stimulation of macrophages and spleen cells;
b) providing aminosugars for incorporation into glycosaminoglycans of newly formed connective tissues;
c) favouring diffusion of factors and other compounds, cell proliferation and epithelial cell migration, in view of the gel forming ability of 5-methylpyrrolidinone chitosan in the boundary regions in contact with the wound tissues,
d) preventing regression to a vascular scar tissue.

As far as macrophage activation by oligomers generated from 5-methylpyrrolidinone chitosan is concerned, activation means production of interleukin-1 which promotes fibroblast proliferation, leading to ordered collagen deposition. The teaching from cited prior art [Malette and Quigley] appears to be misleading in this report.

Activated macrophages also secrete interferon and tumor necrosis factor which provide a favourable situation for the further production of N-acetylglucosaminidase isoenzymes capable to hydrolyze the above mentioned oligomers to monomers. The latter become available for incorporation into hyaluronic acid, keratan sulfate and chondroitin sulfate via the well known biosynthetic route of these macromolecules. Thus, on one hand, 5-methylpyrrolidinone chitosan favours ordered collagen fibril formation rather than disordered scar tissue deposition, which is an essential condition for imparting functionality to the repair tissue; and on the other hand, creates the biochemical conditions for the availability of aminosugars, i.e., building blocks of the polysaccharides present in the extracellular matrix. These two combined actions, which are unique to 5-methylpyrrolidinone chitosan, according to the present invention, explain the efficacy and the usefulness of 5-methylpyrrolidinone chitosan in wound treatment. The presence of said compounds in the wound site also explains the angiogenetic action and absence of inflammation.

According to the favourable properties of 5-methylpyrrolidinone chitosan, this material may be advantageously used in wound dressing materials, e.g. in the form of freeze-dried materials, powders, films, nonwoven fabrics, adhesive tapes, bandages, membranes, solutions, xerogels, hydrogels, filaments, textiles, tissues, lotions, creams. Such wound dressings are intended for internal and external use, to heal burns from heat and solar radiation, surgical and traumatic wounds, infections and decubitus ulcers.

Due to the same reasons, it may be used as well as cosmetic ingredient, e.g. in the form of freeze-dried materials, powders, films, membranes, solutions and gels. These cosmetic ingredients are suitable as such, to form facial masks or to be used as cosmetic applicators, or are to be formulated into emulsions, shampoos, haircare preparations, gels, liquid crystal compositions, liposomes, mainly to confer functional properties to the final preparations, or more simply to modify their rheology or stabilize certain systems such as liposomes and microemulsions.

Furthermore, it may be applied in coatings, e.g. for prosthetic and orthopaedic devices, manufactured with silicones, polyurethanes, hydroxyapatites and other biomaterials. These coatings are mainly intended to confer biocompatibility to the medical items, and to avoid tissue reactions when the latter are implanted.

Finally, it may be applied in supports for delayed release of drugs, e.g. in the form of freeze-dried materials, powders, films, membranes, solutions, gels, filaments, textiles, tissues, lotions, creams, tablets. These excipients for delayed release are mainly intended to enhance water-solubility of poorly soluble drugs and to make such drug available to the organism over an extended period of time after administration.

Advantages of 5-methylpyrrolidinone chitosan over N-carboxybutyl chitosan are the following: 5-methylpyrrolidinone chitosan being deprived of free carboxyl groups has no amphoteric behavior as N-carboxybutyl chitosan has, and therefore is more cationic in character which leads to better antimicrobial action; the lactam rings in 5-methylpyrrolidinone chitosan are capable to prevent hydrogen bond association and therefore 5-methylpyrrolidinone chitosan is also soluble at alkaline pH values whereas N-carboxybutyl chitosan is not; in view of the stability of the lactam ring, 5-methylpyrrolidinone chitosan is more stable in the course of time.

The chemical and technological processes, and the clinical and histological effects which constitute the embodiment of the present invention are given in the following examples, which, however, are not intended to be a limitation of the applicability of this invention.

EXAMPLES

Example 1—Preparation of 5-methylpyrrolidinone chitosan

Crustacean chitosan powder (9 g) was suspended in water (500 g) and kept under stirring for at least 1 hour. Levulinic acid (9.7 g) was then poured into the reaction vessel, and pH became in general 4.3, which is convenient for the Schiff reaction to take place, at 25° C. Sodium borohydrided solution (20 ml, 70 g/l) was delivered over a time period of at least 3 hours, to reach pH 5.6. The resulting solution was dialysed against distilled water for 3 days (3 changes) and used for preparations according to Example 2. In case of medium molecular weight chitosans ($50-100 \times 10^3$ dalton), initial concentration was higher than indicated above, typically 50 g/l. Chitosan concentration, pH values and hydrogenation time, as indicated in this Example, are crucial parameters for the satisfactory preparation of 5-methylpyrrolidinone chitosans. A portion of the product was submitted to analysis according to the above indicated criteria and methods, by infrared spectrometry and nuclear magnetic resonance spectrometry, and found to correspond to the structure of 5-methylpyrrolidinone chitosan.

Example 2—Absence of chelating ability towards lead

Absorption spectra in the ultraviolet region were recorded with the aid of a Varian spectrophotometer by the twin-cells method which permits the chelate spectrum to be recorded with no interference from other absorbing species. This was done on lead perchlorate solutions having concentration 0.06 mol/l in admixture with either 5-methylpyrrolidinone chitosan or N-carboxybutyl chitosan (6 mmol/l). In the latter case, absorption bands centered at 227 nm were recorded and their height was proportional to the molar ratio between lead ion and sugar unit; on the opposite, in the case of 5-methylpyrrolidinone chitosan, a flat spectrum deprived of any absorption band was recorded, thus revealing the different behavior towards metal ions, due to the presence of lactam in 5-methylpyrrolidinone chitosan.

Example 3—Preparation of wound dressings

Aqueous solutions containing 5-methylpyrrolidinone chitosan can be diluted with alcohols, including ethanol and 2-propanol. They are compatible with other polymer solutions including gelatin, poly(vinylalcohol), poly(vinylpyrrolidone) and hyaluronic acid. For the preferred preparation of wound dressing materials, aqueous solutions at pH values close to neutrality, preferably 6, after dialysis, were freeze-dried to yield fleeces. The latter were optionally laminated between stainless steel plates to reduce their thickness to ca. 1-2 mm, and after sealing them in double plastic envelopes, were submitted to $^{60}$cobalt gamma-ray irradiation at 1.4 Mrad. The resulting soft and sterile material could be applied on any surgical or traumatic wound. As an alternative to lyophilization, thermal drying was used: the 5-methylpyrrolidinone chitosan solutions were evaporated preferably at 50° C. on plastic or glass plates. Both procedures were used to coat orthopaedic objects.

Example 4—Uses in plastic surgery

In patients undergoing plastic surgery, donor sites on the front side of the right leg were treated with fleeces of freeze-dried 5-methylpyrrolidinone chitosan to promote ordered tissue regeneration. Compared to controls (left leg of the same patient), better histoarchitectural order, better vascularization and absence of inflammatory cells were observed at the dermal level, while fewer aspects of proliferation of the malpighian layer were reported at the epidermal level.

In the late stages of the normal process of the wound healing, when collagen synthesis declines and high oxygen tension is no longer required, many new vascular channels regress: the wound becomes usually avascular and undergoes transformation into a scar with limited tissue elasticity. Regression of angiogenesis took place in all cases as soon as 5-methylpyrrolidinone chitosan was no longer administered or had been absorbed; nevertheless, the resulting connective tissue appeared orderly structured and endowed of good functionality. The 5-methylpyrrolidinone chitosan provided a tridimensional supporting lattice favouring the epithelial cell migration, and in any way, modulated re-epithelialization.

Example 5—Use in plastic surgery with insertion of expanders

An aspect of importance in plastic surgery is capsule formation around a foreign body. Anomalous deposition of connective tissue takes place when the dynamic equilibrium between synthesis and breakdown is altered, leading to fibrosis, an ubiquitous, aspecific and disordered increase of collagen. The fibrous capsule formed after implanting a tissue expander under the skin is a macroscopic aspect of such reparative process. The connective tissue cellular components responsible for the organization of the collagen lattice, determine such a structure by exerting oriented fraction forces. Steps leading to capsular structure are:

1) mesenchymal elements are attracted and concentrated were the attraction is stronger and increase it;
2) fibroblasts aligned along the major axis of the extracellular fiber bundles tend to orientate the fiber along the axis, thus amplifying the process of structural orientation.

Silicone expanders coated with 5-methylpyrrolidinone chitosan were inserted into surgical wounds, and the formation of capsular tissue was studied by electron microscopy. During all of the stems of capsular organization, 5-methylpyrrolidinone chitosan sustained correct proliferation and organization, and stimulated physiologically the tissue repair process; angiogenesis was favoured while fibrogenesis was depressed.

The formation of vascularized connective tissue with copious mesenchymal elements and reduced collagen components indicated the ability of 5-methylpyrrolidinone chitosan to assist newly formed tissue in retaining good trophicity and loose state, which are favourable physiological characteristics. 5-methylpyrrolidinone chitosan increased the interfibrillar amorphous substance in the dermal region close to the expander, and reduced the damage generated by the foreign body. The loose capsular tissue formed in its presence was less prone to contraction-retraction, during maturation.

Example 6—Use in orthopedics

The well-known difficulties in obtaining spontaneous repair of the meniscal structure are a real challenge to the use of biomaterials intended for promotion of a guided repair of the carthilagineous tissue.

The angiogenetic properties of 5-methylpyrrolidinone chitosan assumed particular importance in the repair process of the meniscus. In fact, such repair is conditioned by the presence of vessels that 5-methylpyrrolidinone chitosan could be able to extend from adjacent capsular structure. Results indicated that 5-methylpyrrolidinone chitosan was well tolerated at the articular-synovial level. It also favoured and stimulated the repair processes which do not take place spontaneously in the meniscus.

In the meniscal areas close to the synovial lining, the angiogenetic stimulus provided by 5-methylpyrrolidinone chitosan led to further repair processes of the meniscal tissue as indicated by morphological data. Repair did not take place when the surgical lesion was excessively distant from the vascular structure of the meniscus-synovium junction. Observations made on the synovium 45 days after the application of 5-methylpyrrolidinone chitosan, showed that the synovial membrane had cells layered on a subintimal stromal tissue exhibiting tightly packed collagen fibers among which mesenchymal cells and vascular structures were visible. After the same number of days, the meniscal tissue was characterized by structural reparative aspects with irregularly distributed collagen bundles, evolving toward cartilagineous tissue; microvessels were also present. In conclusion, 5-methylpyrrolidinone chitosan was found suitable for healing meniscal lesions.

Example 7—Use in dental surgery

Osteoinduction is a phenomenon leading to growth of capillaries, perivascular tissue and bone-generating cells, proceeding from the bottom of the alveolar bed and invading most of the space occupied by 5-methylpyrrolidinone chitosan. Surgical wounds produced in order to remove the apical part of an infected tooth, or to remove in toto a wisdom tooth were filled with freeze-dried 5-methylpyrrolidinone chitosan. At the x-ray examination, one month after surgery, the formation of native bone was evident in all the 6 patients treated. Biopsies taken on 2 patients 4 months after surgery, and examined at the electron microscope, confirmed the generation of bone tissue in the alveolar region, which filled the space occupied by 5-methylpyrrolidinone chitosan. As a consequence, functionality of the same tooth (apicectomy) and of the adjacent teeth (extraction of wisdom tooth) was much improved, in comparison to control patients treated in traditional way. In no case inflammation took place to extents exceeding the normal inflammation for controls.

Example 8—Use in Gerontology

In aging skin, collagen undergoes cross-linking reactions and physico-chemical alterations; proteoglycans decrease in general and their percent ratios are altered. Vascular walls undergo thickness increase and a reduced quantity of oxygen reaches the cutaneous tissue with unfavourable consequences in case of ulcers and burns. Hypertension, oedema, atherosclerosis and diabetes further reduce the quantity of oxygen, nutrients and cells having defensive action (leukocytes and macrophages) reaching the cutaneous tissue.

Patients (10, average age 62) suffering from leg ulcers were submitted to treatment with 5-methylpyrrolidinone chitosan fleeces or gels, for periods of time up to 30 days. Compared to controls, a more rapid epithelialization was remarked (7 days instead of 15–20 days). In no case infections occurred and good hemostasis was observed. From the morphological point of view, controls showed the usual disordered deposition of collagen fibers, whilst in patients treated with 5-methylpyrrolidinone chitosan, a correct histoarchitecture of the regenerated skin was observed, in particular an ordered organization and vascularization of the derma.

Example 9—Preparation of cosmetic facial masks

Facial masks were prepared by pouring a solution (400 g, 16 g/l) of freshly prepared 6-methylpyrrolidinone chitosan on a flat polystyrene or glass surface (20×30 cm) and drying at 50° C. in a ventilated oven for 12 hours. The 5-methylpyrrolidinone chitosan masks were also prepared with the addition of ethoxylated castor oil as a plasticizer (5%). The transparent films thus obtained had the peculiar characteristic of forming a gel when contacted with water. Therefore, when contacted with moisturized facial skin, the facial masks partially gelified on the contact side and fully adhered to the skin. A group of persons (5 ladies) participating in the evaluation of these masks reported unanimously that the application was comfortable and pleasant, due to complete and durable adhesion, agreeable refreshing feeling and attractive transparency. After removal, effective skin cleaning and a durable moisturizing effect were reported. Advantages over collagen masks were: transparency, full adhesion, gel-forming ability and long-lasting effect.

Example 10—Preparation of cosmetic creams

Oil-in-water emulsions were prepared to contain: Xalifin-15 ® [ethoxylated fatty acids $C_{12-18}$], 4.5 g; Glucamate SS20 ® [methylclucoside stearate, ethoxylated], 5.4 g; Glucate SS ® [methylglucoside stearate], 3.6 g; Cetyl alcohol [n-esadecanol], 13.5 g; Cetiol ® [oleyl oleate], 45.0 g; Karité butter, 9.0 g; Water, 315 g; Gram-1 ® [imidazolinyl urea], 1.25 g; Kathon-CG ® [isothiazolinone chloride], 0.75 g. This formulation was taken as a reference. By replacing a portion of water (125 g) with as much 5-methylpyrrolidinone chitosan 1% solution, a cream was obtained with superior organoleptic characteristics, filmogenicitiy, hydrating capacity and skin-protective action. The rheological behavior were typical for plastic systems. The presence of 5-methylpyrrolidinone chitosan did not alter the sensitivity of the cream no the deformation, but promoted restructuring after mechanical stress. Ultraviolet irradiation yielded very modest chromatic variations.

I claim:

1. A modified chitin and/or chitosan polymer consisting essentially of monomeric units of formula I

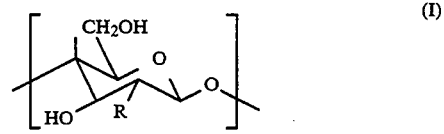

wherein
R is $—NH_2$, $—NHCOCH_3$ or R', wherein
R' is an open chain N-carboxybutyl group or the isomeric cyclic 5-methylpyrrolidinone group of formula II

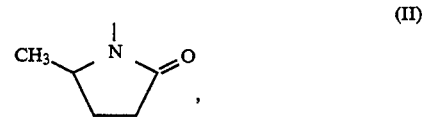

wherein 90% of R' is present as the 5-methylpyrrolidinone of
formula II; and wherein said monomeric units of formula I wherein R is R' comprise at least 30% of the total monomeric units in the modified chitin and/or chitosan polymer.

2. A wound dressing material made in whole or in part with a polymer of claim 1, in the form of a freeze-dried material, powder, film, non-woven fabric, adhesive tape, bandage, membrane, solution, xerogel, hydrogel, filament, textile, tissue, lotion or cream.

3. A support for delayed release of a drug made in whole or in part with a polymer of claim 1, in the form of a freeze-dried material, powder, film, membrane, solution, gel, filament, textile, tissue, lotion, cream or tablet.

4. A cosmetic ingredient made in whole or in part with a polymer of claim 1, in the form of a freeze-dried material, powder, film, membrane, solution or gel.

* * * * *